United States Patent
Ueno et al.

(10) Patent No.: US 9,875,873 B2
(45) Date of Patent: Jan. 23, 2018

(54) PARTICLE CHARGER

(71) Applicant: SHIMADZU CORPORATION, Kyoto-shi, Kyoto (JP)

(72) Inventors: Yoshihiro Ueno, Uji (JP); Hiroshi Seki, Kyotanabe (JP); Hiroshi Okuda, Nagaokakyo (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/501,935

(22) PCT Filed: Aug. 8, 2014

(86) PCT No.: PCT/JP2014/071078
§ 371 (c)(1),
(2) Date: Feb. 6, 2017

(87) PCT Pub. No.: WO2016/021063
PCT Pub. Date: Feb. 11, 2016

(65) Prior Publication Data
US 2017/0229275 A1   Aug. 10, 2017

(51) Int. Cl.
*H01J 27/02* (2006.01)
*H01J 49/12* (2006.01)
(Continued)

(52) U.S. Cl.
CPC ............ *H01J 27/024* (2013.01); *G01N 27/62* (2013.01); *H01J 37/321* (2013.01);
(Continued)

(58) Field of Classification Search
CPC .......... H01J 37/32009; H01J 37/32082; H01J 37/321; H01J 37/32357; H01J 37/3244; H01J 37/32532; H01J 49/26; H01J 49/405
See application file for complete search history.

(56) References Cited

U.S. PATENT DOCUMENTS 5,102,523 A * 4/1992 Beisswenger ..... H01J 37/32009
                                                    118/723 E
6,444,137 B1 * 9/2002 Collins ................. C23C 16/402
                                                    216/67
(Continued)

FOREIGN PATENT DOCUMENTS

JP    2007-305498 A    11/2007
JP    4905040 B2        3/2012

OTHER PUBLICATIONS

Yoshihiro Sato et al., "The Relation between the Charged Fractions of the Aerosol Charge Neutralizer and the Time Change of the Ion Mobility", J. Inst. Electrostat. Jpn., 2011, pp. 14-19, vol. 35, No. 1.
(Continued)

*Primary Examiner* — Tung X Le
(74) *Attorney, Agent, or Firm* — Sughrue Mion, PLLC (57) ABSTRACT

A particle charger is provided with: a filter (28) partitioning the inside of a housing (20) into a first space (29) and second space (30); a particle introducer (22) for introducing a particle into the first space; a gas ion supplier (10) for supplying the first space with a gas ion; a potential gradient creator (26, 27, 31) for creating a potential difference within the housing so as to make the gas ion and a charged particle resulting from a contact of the aforementioned particle with the gas ion move toward the second space; an AC voltage supplier (32, 33) for applying AC voltages having a phase difference to the neighboring electrodes (28a, b) included in the filter; a controller (35) for performing a control for applying, to the plurality of electrodes, predetermined voltages so as to allow the charged particle to pass through a gap between the electrodes while trapping the gas ion by the electrodes; and a charged particle extractor (23, 25, 34) for extracting the charged particle admitted to the second space to the outside of the housing. By this configuration, the occurrence frequency of the multi-charging is suppressed.

12 Claims, 6 Drawing Sheets

(51) Int. Cl.
G01N 27/62 (2006.01)
H01J 37/32 (2006.01)

(52) U.S. Cl.
CPC .... *H01J 37/32009* (2013.01); *H01J 37/3244* (2013.01); *H01J 37/32082* (2013.01); *H01J 37/32357* (2013.01); *H01J 37/32532* (2013.01); *H01J 49/12* (2013.01)

(56) References Cited

U.S. PATENT DOCUMENTS

| | | | |
|---|---|---|---|
| 2004/0221958 A1* | 11/2004 | Loewenhardt .... | H01J 37/32082 156/345.47 |
| 2005/0189484 A1* | 9/2005 | Glukhoy ............ | H01J 49/0445 250/287 |
| 2009/0095714 A1* | 4/2009 | Chen ..................... | H01J 37/321 216/67 |
| 2012/0043460 A1* | 2/2012 | Wouters ............. | H01J 49/0404 250/282 |

OTHER PUBLICATIONS

International Search Report of PCT/JP2014/071078 dated Nov. 11, 2014.
Written Opinion for PCT/JP2014/071078 dated Nov. 11, 2014. [PCT/ISA/237].

* cited by examiner

PARTICLE CHARGER

CROSS REFERENCE TO RELATED APPLICATIONS

This application is a National Stage of International Application No. PCT/JP2014/071078, filed Aug. 8, 2014, the contents of which are incorporated herein by reference in its entirety.

TECHNICAL FIELD

The present invention relates to a particle charger for electrically charging microparticles in a gas.

BACKGROUND ART

Micro-sized liquid or solid particles suspended in a gas are generally called aerosols. Most of the contaminants contained in the exhaust gas of automobiles or in the smoke emitted from manufacturing plants are aerosols. In particular, aerosols with a particle diameter smaller than 1 µm, or so-called "nano-aerosols", have raised concerns about their unfavorable influences on health. Therefore, measuring their particle diameters or distribution of particle diameters has been extremely important in such areas as environmental measurement and assessment. As a device for measuring the particle-diameter distribution of aerosols (particle classifier), a differential mobility analyzer (DMA), which classifies microparticles using the difference in the moving speed of charged microparticles within an electric field (electric mobility), has been popularly used (see Patent Literature 1 or other documents).

In a measurement using a DMA, the particles to be subjected to the measurement (aerosols) need to be electrically charged in advance of the measurement. To this end, several types of particle chargers have been conventionally used. A comparatively traditional type of particle charger is one which uses alpha rays emitted from americium (Am), beta rays emitted from krypton (Kr) or similar radiations as the ion source and forces the ions generated by this ion source to come in contact with the particles as the charging target to electrically charge those particles (see Non Patent Literature 1). This device is also called the "bipolar diffusion neutralizer", or simply "neutralizer".

However, this type of particle charger has problems associated with the use of the radiation source, such as the necessity of being operated with the greatest concern for safety as well poor portability. Accordingly, in recent years, as a substitute for this particle charger, a particle charger using an ion source which employs electric discharge, such as corona discharge, has been increasingly used. For example, as described in Patent Literature 2, this type of particle charger ionizes an appropriate kind of carrier-gas molecules by corona discharge or similar electric discharge and forces the generated ions to come in contact with sample particles as the charging target to electrically charge those particles.

Figure 8:
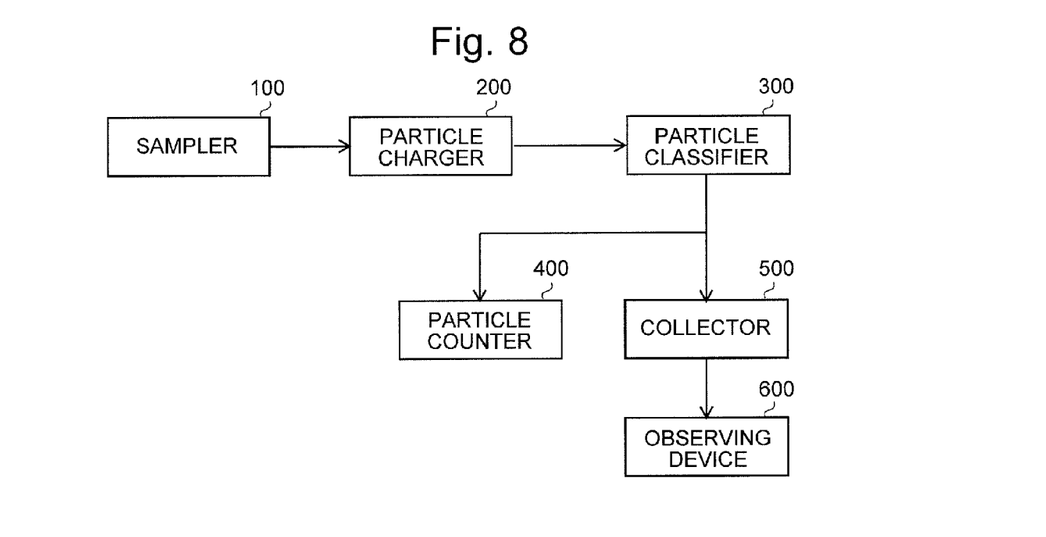
FIG. 8 is a block diagram showing one example of the particle classifying and observing system.

FIG. 8 shows one example of the configuration of a particle classifying and observing system including the previously described type of particle charger along with a particle classifier. In this particle classifying and observing system, the particles (aerosols) as the measurement target collected with a sampler 100 are sent into the particle charger 200, which electrically charges those particles and sends them to the particle classifier 300. The charged particles sent to the particle classifier 300 are classified according to the difference in their electrical mobilities. After that, those particles are sent to a particle counter 400 so as to be counted per particle diameter, or are collected with a collector 500 so as to be observed through an observing device 600.

CITATION LIST

Patent Literature

Patent Literature 1: JP 4905040 B
Patent Literature 1: JP 2007-305498 A

Non Patent Literature

Non Patent Literature 1: Sato, Sakurai and Ehara, "The Relation between the Charged Fractions of the Aerosol Charge Neutralizer and the Time Change of the Ion Mobility", *J. Inst. Electrostat. Jpn.*, Vol. 35, No.1, 2011, pp. 14-19

SUMMARY OF INVENTION

Technical Problem

In the previously described particle charger, it is necessary to equalize the number of charges (valence) of the sample particles in order to improve the classifying accuracy in the particle classifier located in the subsequent stage. However, in general, large-sized particles (heavy particles) are likely to vary in their valence due to the frequent occurrence of multi-charging.

The present invention has been developed in view of the aforementioned point. Its objective is to provide a particle charger which can suppress the occurrence frequency of the multi-charging and thereby equalize the valence of the charged particles.

Solution to Problem

A commonly known reason for the easy occurrence of the multi-charging on the large-sized particles is that large-sized particles have larger surface areas and therefore higher chances of contact with the ions than small-sized particles. Additionally, there is another possible reason: Larger particles move slowly in a gas stream, so that they reside within the particle charger for a longer period of time and have higher chances of contact with the ions than smaller particles. Accordingly, the present inventors have carried out intensive research so as to reduce the residence time of the sample particles in the area where the gas ions are present within the particle charger. Consequently, the present invention has been created.

That is to say, the particle charger according to the present invention includes:

a) a housing;

b) a filter composed of a plurality of electrodes extending in a virtual surface partitioning the inside of the housing into a first space and a second space;

c) a particle introducer for introducing a particle to be charged into the first space;

d) a gas ion supplier for supplying the first space with a gas ion;

e) a potential gradient creator for creating a potential gradient within the housing so as to make the gas ion and a charged particle resulting from a contact of the aforementioned particle with the gas ion move from the first space toward the second space;

f) an AC voltage supplier for applying an AC voltage to each of the electrodes forming the filter, where the voltages applied to any two electrodes neighboring each other among the plurality of electrodes have a phase difference;

g) a controller for controlling the AC voltage supplier so as to apply, to the plurality of electrodes, voltages which are previously determined so that, among the charged particle and the gas ion moving from the first space toward the second space, the charged particle is allowed to pass through a gap between the electrodes while the gas ion is trapped by one of the electrodes;

h) a charged particle extractor for extracting the charged particle admitted to the second space to the outside of the housing.

By this configuration, the charged particle generated by coming in contact with the gas ion in the first space moves from the first space toward the second space due to the effect of the potential gradient and eventually reaches the second space through the filter. Although the gas ion is also urged to move from the first space toward the second space, the gas ion is trapped by the filter and cannot reach the second space. In this manner, the charged particle generated within the first space can be promptly transferred into the space where no gas ion is present, i.e. the second space. As a result, the contact time between the gas ion and the particle to be charged is reduced, so that the occurrence of the multi-charging is suppressed.

Specifically, for example, in the particle charger according to the present invention, the relationship between the diameter of the particle to be charged and the suitable voltages to be applied to the filter for trapping the gas ion while allowing the passage of the charged particle (e.g. amplitude, frequency, phase difference between the neighboring electrodes, etc.) is experimentally investigated and stored beforehand. When the target diameter of the particle to be charged is specified, the controller determines the application voltages corresponding to that target diameter with reference to the stored information, and controls the AC voltage supplier so that the determined voltages skill be applied to the electrodes forming the filter.

The "virtual surface" in the present invention may be a flat surface or curved surface. The gas supplier may introduce, into the first space, gas ions produced at a different location, or it may generate gas ions within the first space. The AC voltage supplier may apply a sinusoidal voltage or non-sinusoidal voltage (e.g. rectangular voltage) to each electrode as the AC voltage. Applying a rectangular voltage has the advantage of facilitating the frequency change, duty-cycle control, phase control and other operations on the AC voltage, since rectangular voltages can be generated by turning a DC voltage on and off using a semiconductor switching element.

The shape of the filter is not specifically limited. For example, it may be composed of a plurality of rod electrodes arranged parallel to each other, or a plurality of rod electrodes arranged in the form of a grid. A concentric arrangement of a plurality of circular electrodes is also possible.

The charged particle extractor can be configured, for example, so as to produce a stream of gas in a direction intersecting with the direction from the first space toward the second space, and extract the charged particle from the housing to the outside by this stream of gas.

The charged particle extractor can also be configured so as to create a potential gradient in a direction intersecting with the direction from the first space toward the second space, and extract the charged particle from the housing to the outside by using the motion of the charged particle along the potential gradient.

Advantageous Effects of the Invention

As described to this point, the particle charger according to the present invention can suppress the multi-charging and increase the ratio of the singly-charged particles.

DESCRIPTION OF EMBODIMENTS

Figure 1A:
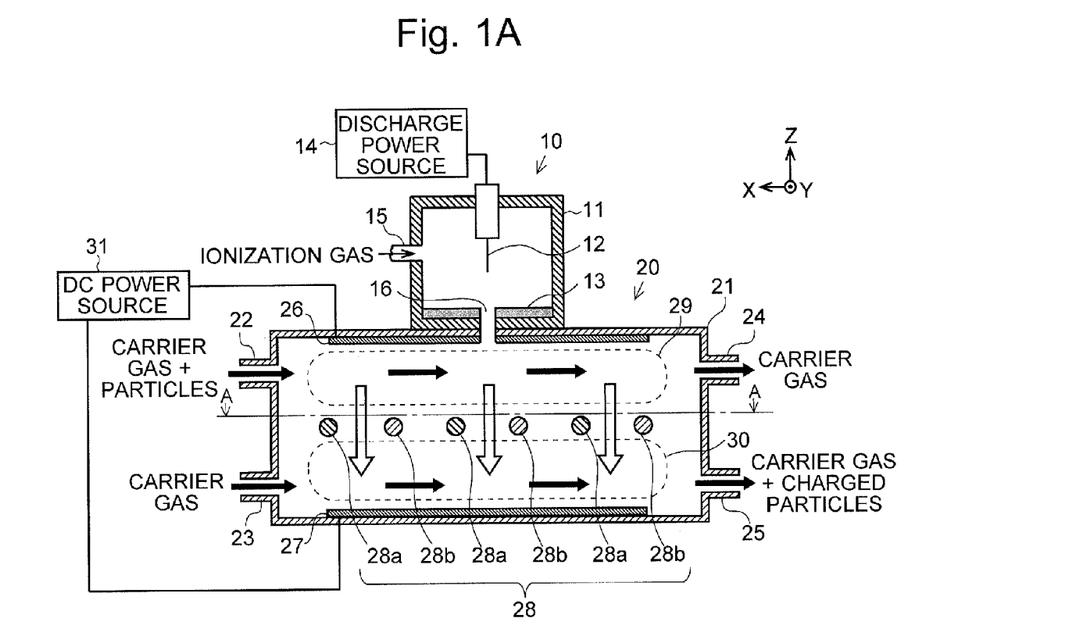
FIG. 1A is a model diagram showing a vertical section of a particle charger according to one embodiment of the present invention.
Figure 1B:
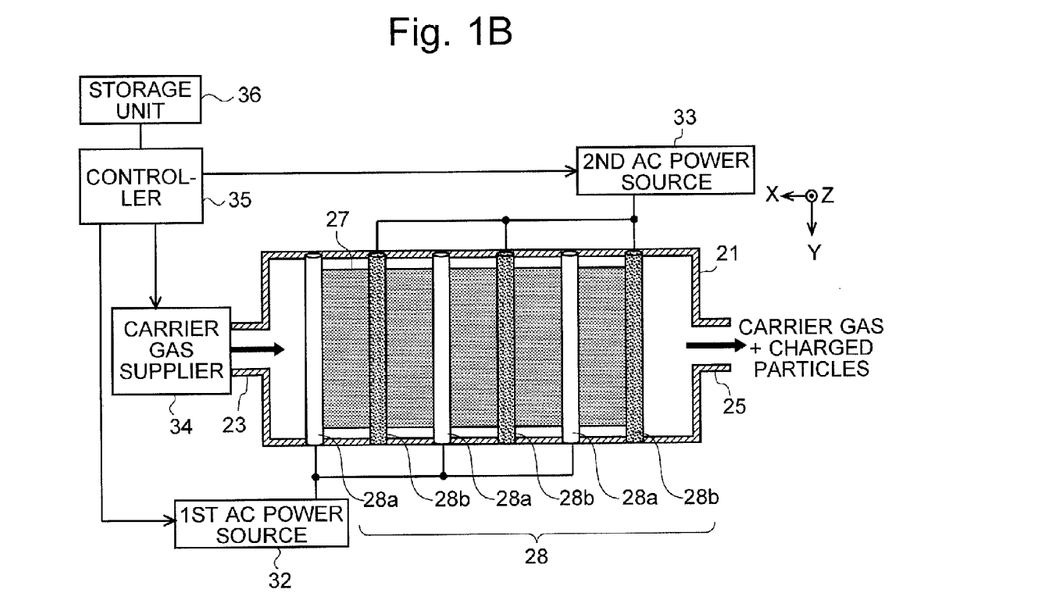
FIG. 1B is a section viewed along the arrows A-A in FIG. 1A.
Figure 2:
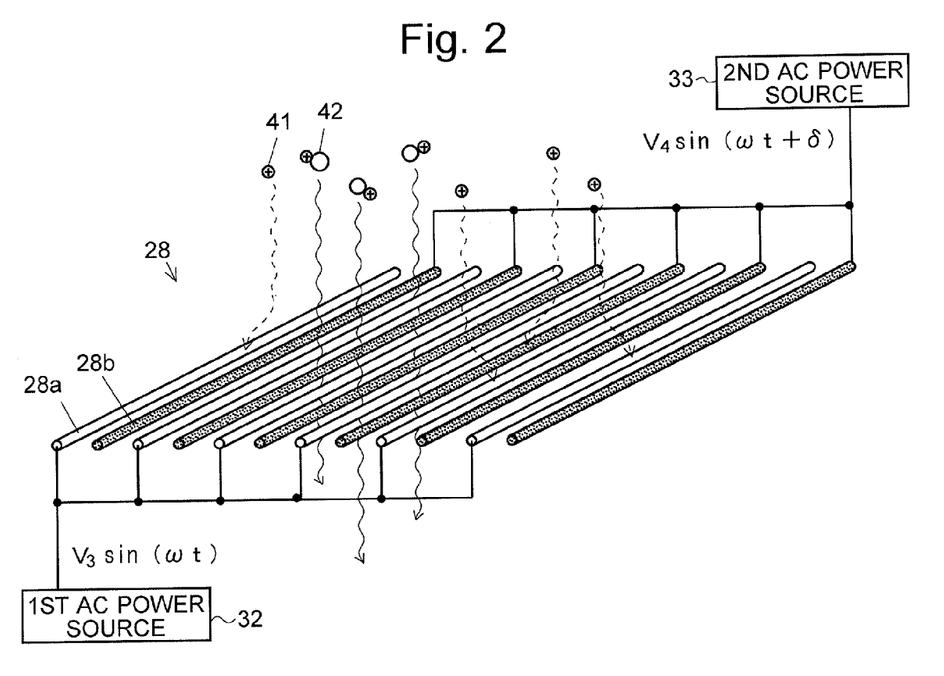
FIG. 2 is a diagram illustrating the principle of separating charged particles from gas ions by a filter.

Modes for carrying out the present invention are hereinafter described with reference to the drawings. FIGS. 1A and 1B are schematic configuration diagrams of a particle charger according to the present embodiment, where FIG. 1A shows a vertical section of the particle charger, and FIG. 1B shows a section viewed along the arrows A-A in FIG. 1A. FIG. 2 is a perspective view of the filter in the same particle charger. It should be noted that the front-rear, up-down, and right-left directions mentioned in the following descriptions are defined so that the X, Y and Z directions in FIG. 1A correspond to the leftward, frontward and upward directions, respectively.

The particle charger according to the present embodiment, which is designed to be placed between the sampler 100 and the classifier 300 in a particle classifying and observing system as shown in FIG. 8, includes a particle-charging unit 20 and a gas-ion generating unit 10 (which corresponds to the gas ion supplier in the present invention) located above the former unit.

The particle-charging unit 20 has a substantially rectangular parallelepiped chamber 21 (which corresponds to the housing in the present invention). On the left wall of this chamber 21, a first upward-side opening 22 (which corresponds to the particle introducer in the present invention) and a second upward-side opening 23 are vertically arranged, both of which are the openings for allowing an inflow of gas from the outside into the chamber 21. On the right wall of the chamber 21, a first downward-side opening 24 and a second downward-side opening 25 are vertically arranged, both of which are the openings for discharging gas from the chamber 21 to the outside. This chamber 21 contains a first plate electrode 26 arranged along the top face of the chamber 21, a second plate electrode 27 arranged along the bottom face of the chamber 21, and a filter 28 located between the first and second plate electrodes 26 and 27. This filter 28 is composed of a plurality of rod electrodes 28a and 28b arranged parallel to each other and at regular intervals in a plane parallel to the first and second plate electrodes 26 and 27, with each rod electrode extending in the front-rear direction. Actually, the filter 28 is composed of a large number of electrodes 28a and 28b, as shown in FIG. 2. However, for simplicity, only six electrodes 28a and 28b are shown in FIGS. 1A and 1B. Hereinafter, the space between the first plate electrode 26 and the filter 28 is called the "first space 29", while the space between the filter 28 and the second plate electrode 27 is called the "second space 30".

Provided outside the chamber 21 of the particle-charging unit are a DC power source 31 for applying voltage $V_1$ to the first plate electrode 26 and voltage $V_2$ to the second plate electrode 27, as well as a first AC power source 32 and a second AC power source 33 for applying AC voltages to the electrodes forming the filter 28. The first and second AC power sources 32 and 33 correspond to the AC voltage supplier in the present invention. The first plate electrode 26, second plate electrode 27 and DC power source 31 cooperating with each other function as the potential gradient creator in the present invention. The first AC power source 32 supplies AC voltage $V_3 \sin(\omega t)$ to the electrodes 28a located at the odd-numbered positions as counted from the left end among the large number of electrodes 28a and 28b forming the filter 28. On the other hand, the second AC power source 33 supplies AC voltage $V_4 \sin(\omega t+\delta)$, which has a phase difference of $\delta$ from the AC voltage supplied by the first AC power source 32, to the electrodes 28b located at the even-numbered positions as counted from the left end among the large number of electrodes. There is no specific limitation on the phase difference $\delta$, although a value within a range of 90° to 270° is preferable. The amplitudes $V_3$ and $V_4$, frequency $\omega$, as well as phase difference $\delta$ of the AC voltages supplied by the first and second AC power sources 32 and 33 are controlled by a controller 35. The controller 35 also operates the aforementioned DC power source 31 and a discharge power source 14 (which will be described later), although the control lines for these devices are omitted from the figure for simplicity.

The gas-ion generating unit 10 also has a substantially rectangular parallelepiped chamber 11, which contains a needle-shaped discharge electrode 12 vertically extending downward from the top face. Located on the inner bottom of the same chamber 11 is a plate-shaped ground electrode 13 which forms a pair with the discharge electrode 12. Outside the chamber 11, a discharge power source 14 for applying a voltage for inducing electric discharge to the discharge electrode 12 is provided. Additionally, a gas introduction port 15 for introducing a gas for gas-ion generation ("ionization gas") into the chamber 11 is formed on the side wall of the chamber 11, while an opening for allowing an outflow of the ions generated within the chamber 11 (those ions are hereinafter called the "gas ions") into the first space 29 is formed in the bottom wall of the chamber 11 The ground electrode 13, top wall of the chamber 21 of the particle-charging unit 20, and first plate electrode 26 are also provided with through-holes formed at the position corresponding to the aforementioned opening. The opening and those through-holes form a gas-ion discharge port 16 through which the inner space of the chamber 21 of the particle-charging unit 20 communicates with that of the chamber 11 of the gas-ion generating unit 10.

In the process of generating charged particles by the particle charger according to the present embodiment, an ionization gas (e.g. air) is initially introduced from the gas introduction port 15 into the chamber 11 of the gas-ion generating unit 10, and a voltage is applied from the discharge power source 14 to the discharge electrode 12. As a result, electric discharge occurs in the space between the discharge electrode 12 and the ground electrode 13, whereby the ionization gas within the chamber 11 is ionized. The polarity of the thereby generated gas ions depends on the polarity of the voltage applied to the discharge electrode 12. In the following description, it is assumed that the gas ions are positive ions. The gas ions generated in the gas-ion generating unit 10 flow through the gas-ion discharging port 16 into the first space 29 in the particle-charging unit 20.

Meanwhile, the particles collected as the charging target by the sampler 100 (FIG. 8) in the previous stage and carried by a carrier gas (e.g. air) are introduced from the first upward-side opening 22 into the first space 29. Simultaneously, a carrier gas supplied from a carrier gas supplier 34 (which does not contain the aforementioned particles) is introduced through the second upward-side opening 23 into the second space 30. As a result, a stream of carrier gas, directed from left to right, is formed within each of the first and second spaces 29 and 30 of the chamber 21 (as indicated by the thick black arrows in FIG. 1A). The carrier gas supplier 34, second upward-side opening 23 and second downward-side opening 25 correspond to the charged particle extractor in the present invention.

Since the first space 29 contains gas ions at a high density, the particles to be charged introduced from the first upward-side opening 22 into the first space 29 come in contact with the gas ions and become positively charged by receiving electric charges from the gas ions.

Due to the voltage application by the DC power source 31, the potential $V_1$ of the first plate electrode 26 is higher than the potential $V_2$ of the second plate electrode 27, i.e. $V_1 > V_2$, whereby a potential gradient whose level decreases in the direction indicated by the thick white arrows in FIG. 1A is formed between the two electrodes. Since both the gas ions introduced into the first space 29 and the particles electrically charged within the first space 29 (which are hereinafter called the "charged particles") are positively charged, they follow the potential gradient and move downward (i.e. toward the second space 30) within the chamber 21.

Meanwhile, the filter 28 provided between the first and second spaces 29 and 30 is supplied with the AC voltages whose phases differ from each other between any two electrodes 28a and 28b neighboring each other in the right-left direction. Therefore, the gas ions and charged particles which attempt to pass through the gap between the two electrodes 28a and 28b while moving downward within the chamber 21 in the previously described manner alternately experience attractive and repulsive forces from the electrodes 28a and 28b on both sides. In this process, an object having a comparatively high mobility (which is a value representing how easily a charged particle can move in an electric field) is quickly attracted to and collides with one of the electrodes, failing to pass through the gap between the two electrodes. By comparison, an object having a comparatively low mobility is attracted toward the opposite direction due to the attractive force from the other electrode before it collides with one of the electrodes. Therefore, this object can pass through the gap between the two electrodes 28*a* and 28*b*, oscillating in the right-left direction in a stable manner.

The charged particles generated by the particle charger in the present embodiment have sufficiently lower mobilities than the gas ions. Accordingly, by appropriately adjusting the values related to the conditions (amplitude, frequency and phase difference) of the voltages applied by the first and second AC power sources 32 and 33, it is possible to realize the situation that only the charged particles are allowed to pass through the filter 28 and reach the second space 30 while the gas ions are trapped by the filter 28 and prevented from reaching the second space 30. In other words, as shown in FIG. 2, the charged particles 42, whose mobility is relatively low oscillate in a stable manner and pass through the gaps between the neighboring electrodes 28*a* and 28*b*, to successfully reach the second space 30. On the other hand, the gas ions 41 whose mobility is relatively high, are attracted to and collide with the electrode 28*a* or 28*b* when they come to a certain distance to the filter 28, failing to reach the second space 30.

The conditions of the voltages applied to the filter 28 so as to allow the passage of only the charged particles in the previously described manner are, for example, previously investigated by experiments for each condition (kind, diameter, etc.) of the particles as the charging target and stored in a storage unit 36. When a target particle to be charged is specified by a user, the controller 35 refers to the information stored in the storage unit 36, determines the conditions of the voltages corresponding to the target particle, and controls the first and second AC power sources 32 and 33 so that those voltages are applied to the electrodes 28*a* and 28*b* forming the filter 28.

The charged particles which have reached the second space 30 are carried rightwards within the second space 30 by the stream of carrier gas directed from the second upward-side opening 23 to the second downward-side opening 25. Subsequently, the charged particles are extracted from the second downward-side opening 25 to the outside of the chamber 21 and sent to the particle classifier 300 provided in the subsequent stage (FIG. 8). It should be noted that the amount of voltage applied from the DC power source 31, flow rate of the carrier gas supplied from the carrier gas supplier 34 and other relevant parameters are previously adjusted by the controller 35 so that the charged particles which have passed through the filter 28 and reached the second space 30 will be sent to the outside of the chamber 21 without colliding with the second plate electrode 27.

In this manner, in the particle charger according to the present embodiment, the charged particles generated by coming in contact with the gas ions are promptly extracted to the area where no gas ion is present (the second space 30), whereby the occurrence of the multi-charging is effectively suppressed and the ratio of singly-charged particles is increased. Therefore, in the process of extracting particles having a certain diameter by classification, the mixture of unwanted particles which have different diameters and yet have approximately the same mobility due to the multi-charging is suppressed. Therefore, for example, the accuracy of the particle diameter distribution can be improved, or a high level of collection efficiency can be achieved for particles having a specific particle diameter.

The previously described example is concerned with the configuration in which the gas ions are positive ions and the particles are positively charged by coming into contact with those gas ions. It is also possible to use the opposite configuration in which the gas ions are negative ions and the particles are negatively charged by coming into contact with the gas ions. In this case, the potential $V_1$ of the first plate electrode 26 is set to be lower than the potential $V_2$ of the second plate electrode 27.

In the previous example, the electrodes 28*a* and 28*b* forming the filter 28 are arranged so that they extend in the front-rear direction, i.e. in the orthogonal direction to the stream of the carrier gas. The arrangement is not limited to this form. For example, as shown in FIGS. 3A and 3B, the plurality of electrodes 51*a* and 51*b* forming the filter 51 may be arranged so that they extend in the right-left direction, i.e. in the parallel direction to the stream of the carrier gas.

Figure 3A:
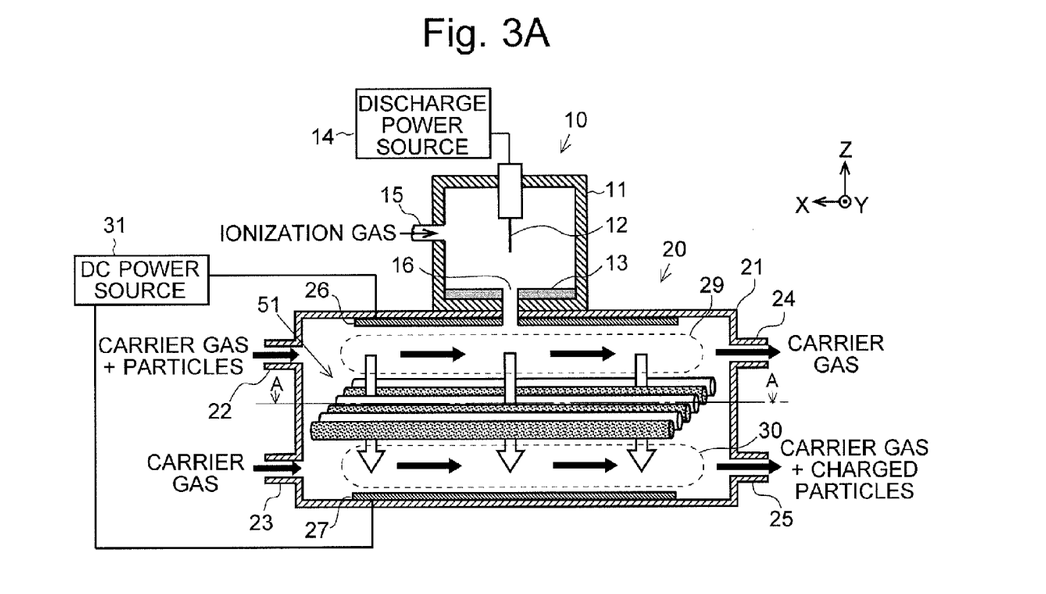
FIG. 3A is a model diagram showing a vertical section of a particle charger according to another embodiment of the present invention.
Figure 3B:
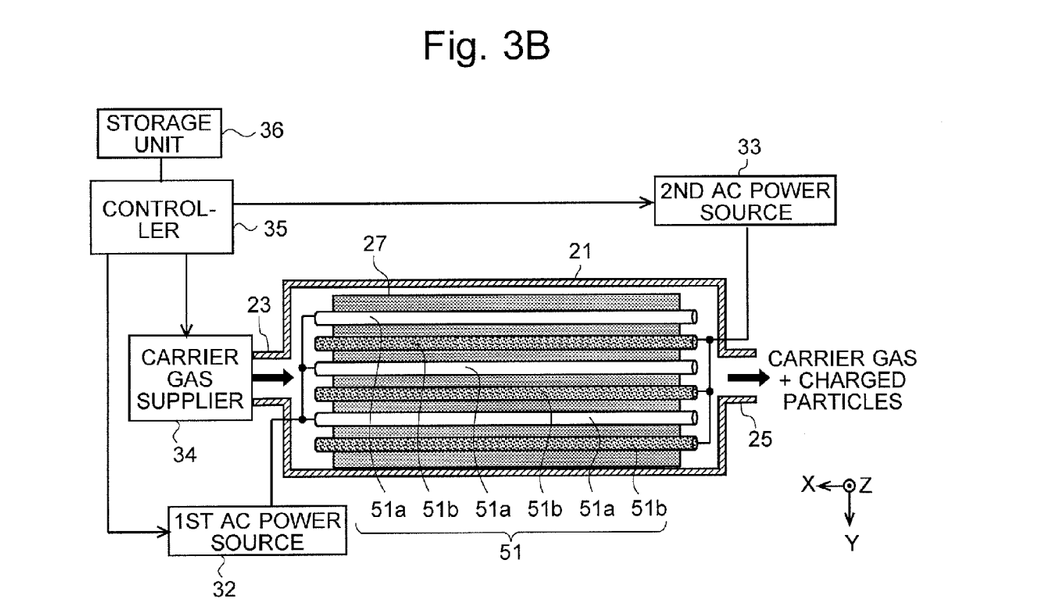
FIG. 3B is a section viewed along the arrows A-A in FIG. 3A.
Figure 4:
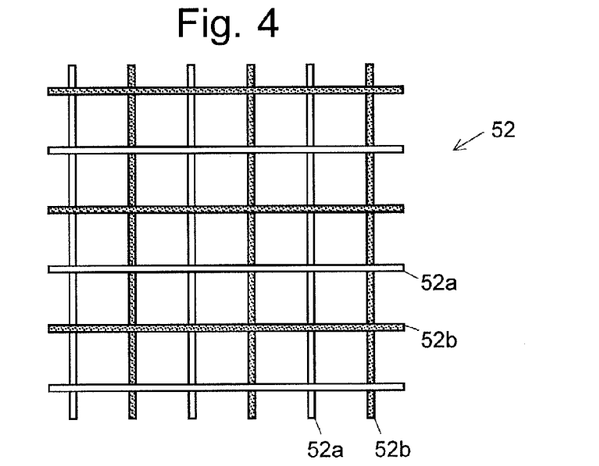
FIG. 4 is a plan view showing an example of the filter in a grid-like form.
Figure 5:
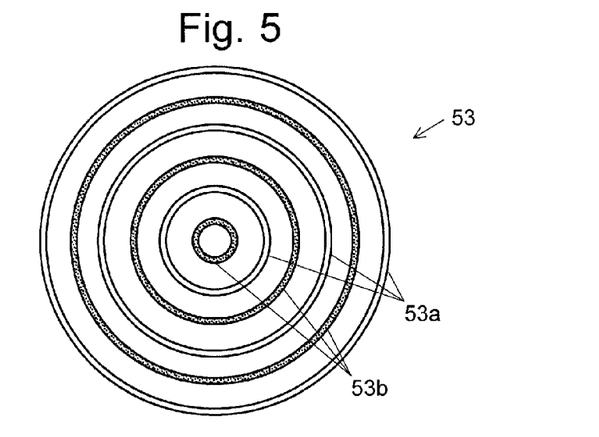
FIG. 5 is a plan view showing an example of the filter in a concentric form.
Figure 6:
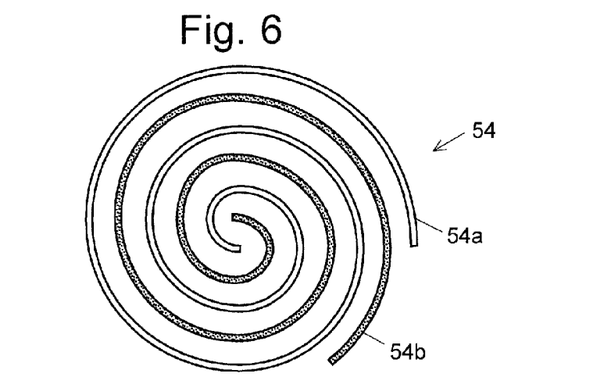
FIG. 6 is a plan view showing an example of the filter in a double spiral form.

Other than the configuration in which straight electrodes are arranged parallel to each other as shown in FIGS. 1A and 1B as well as FIGS. 3A and 3B, for example, the filter may be configured as shown in FIG. 4 in which the filter 52 is composed a plurality of electrodes 52*a* and 52*b* arranged in a grid-like form. In the case of the grid-like form, the electrode group consisting of the vertically arrayed electrodes 52*a* and 52*b* and the one consisting of the horizontally arrayed electrodes 52*a* and 52*b* should be separated from each other in the direction of the electric field created by the first and second plate electrodes 26 and 27 (in the up-down direction in FIG. 1A). It is also possible to use a configuration as shown in FIG. 5, in which the filter 53 is composed of a plurality of circular electrodes 53*a* and 53*b* arranged in a concentric form, or as shown in FIG. 6, in which the filter 54 is composed of a plurality of spiral electrodes 54*a* and 54*b*. In any case, two AC voltages having a phase difference between any two electrodes 52*a* and 52*b*, 53*a* and 53*b*, or 54*a* and 54*b* neighboring each other are applied in the previously described manner.

The cross-sectional shape of each electrode is also not specifically limited. Other than the circular shape as shown in FIGS. 1A and 1B as well as and FIGS. 3A and 3B, it may have a polygonal shape, such as a triangle or quadrangle.

Figure 7:
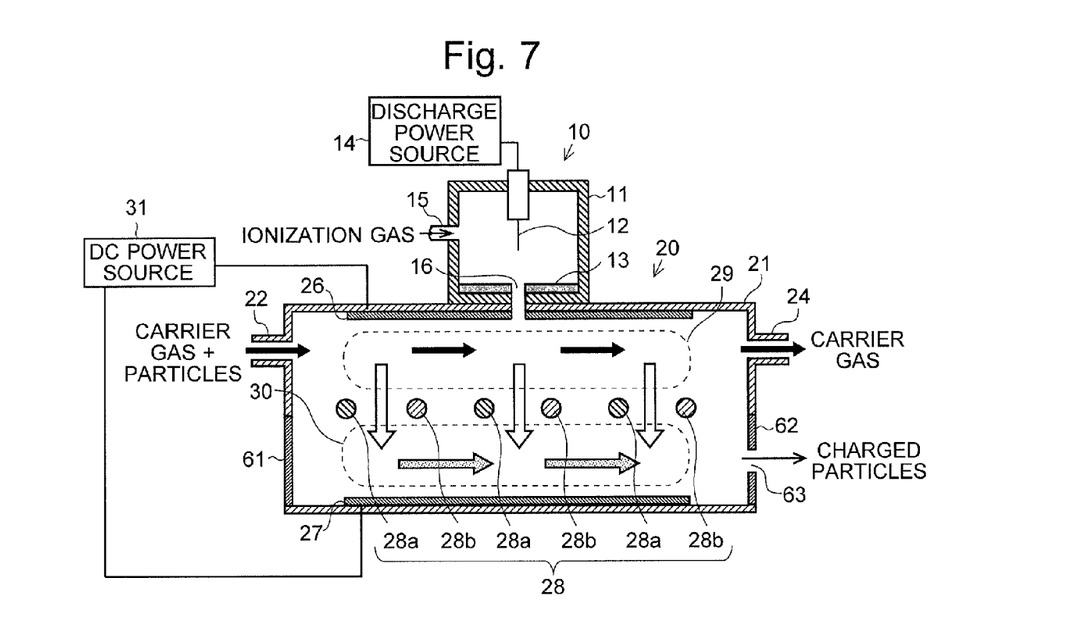
FIG. 7 is a diagram showing a configuration in which the extraction of the charged particles in the present invention is achieved by using a potential difference.

In the previous embodiment, the charged particles which have reached the second space 30 are extracted to the outside of the chamber 21 by a stream of carrier gas. Alternatively, for example, the extraction of the charged particles may be achieved by an extracting electric field created within the second space 30. In this case, as shown in FIG. 7, an extraction electrode 62 and opposite electrode 61 are arranged on the side wall of the chamber 21 of the particle charger 20, facing each other across the second space 30, with a DC voltage applied between the two electrodes to create an extracting electric field having a potential gradient whose level decreases in the direction from the opposite electrode 61 toward the extraction electrode 62 (as indicated by the thick halftone arrows in FIG. 7). According to this configuration, the (positively) charged particles which have passed through the filter 28 and reached the second space 30 in the previously described manner move in the direction from the opposite electrode 61 to the extraction electrode 62 and are eventually extracted from the opening 63 formed in the extraction electrode 62 to the outside of the chamber 21. In place of the plate-shaped electrode having the opening 63 as shown in FIG. 7, a mesh-like electrode may be used as the extraction electrode, with the charged particles extracted through the openings of the mesh. In the case where the charged particles are negatively charged, an extracting electric field having the opposite potential gradient whose level increases from the opposite electrode 61 toward the extraction electrode is created.

Furthermore, the particle extractor in the present invention may also be configured to extract the charged particles by using both the stream of carrier gas and the extracting electric field. In this case, the opposite electrode 61 in FIG. 7 is also be provided with an opening so as to introduce the carrier gas from this opening and thereby create a stream of carrier gas directed from the same opening toward the opening 63 of the extraction electrode.

The particle charger according to the present invention can be applied not only in a particle classifying and observing system as shown in FIG. 8; for example, it can also be used as an ionizing unit in a mass spectrometer.

EXAMPLE

Hereinafter described is a simulation by numerical computation performed to confirm the effect of the particle charger according to the present invention. In this simulation, a system as shown in FIGS. 1A and 1B was simulated under the following conditions: The voltage $V_1$ applied to the first place electrode 26 was 1050 V. The voltage $V_2$ applied to the second place electrode 27 was −1050 V. The AC voltage $V_3 \sin(\omega t)$ supplied from the first AC power source 32 and the AC voltage $V_4 \sin(\omega t+\delta)$ supplied from the second AC power source 33 were set as follows: $V_3=V_4=2000$ V; $\omega=5, 25, 50, 250$ and 500 Hz; and $\delta=\pi$. The electrodes 28a and 28b were 1.0 mm in diameter and arranged at intervals of 15 mm. The gas ions had a mass of 32 Da and a mobility of 1.0E−04 $m^2$/Vs, while the charged particles had a mass of 1.0E+08 Da and a mobility of 2.7E−08 $m^2$/Vs.

Figure 9:
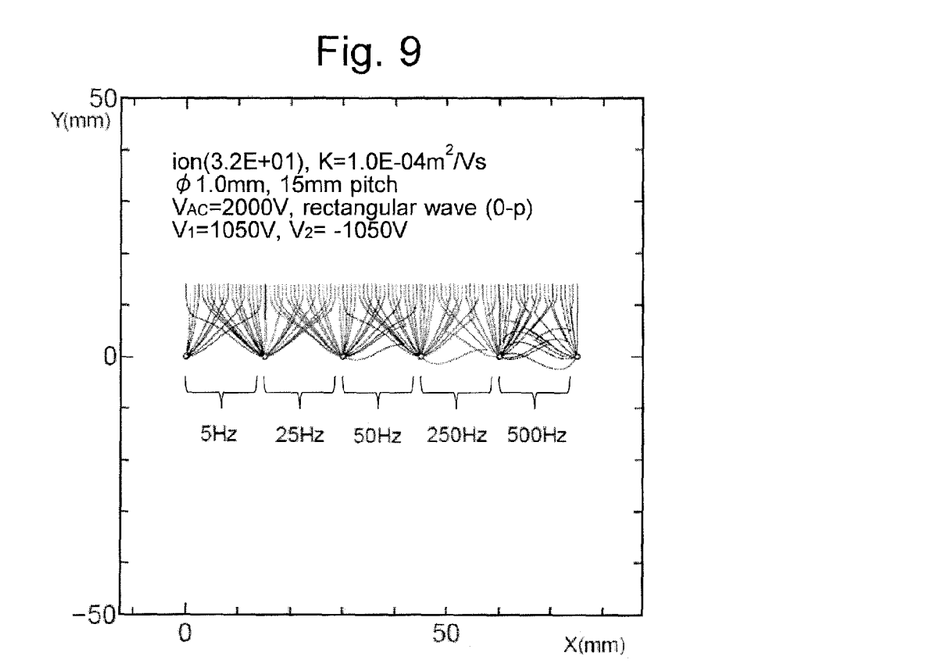
FIG. 9 is a diagram showing the result of a simulation of the trajectory of the gas ion in the present invention.
Figure 10:
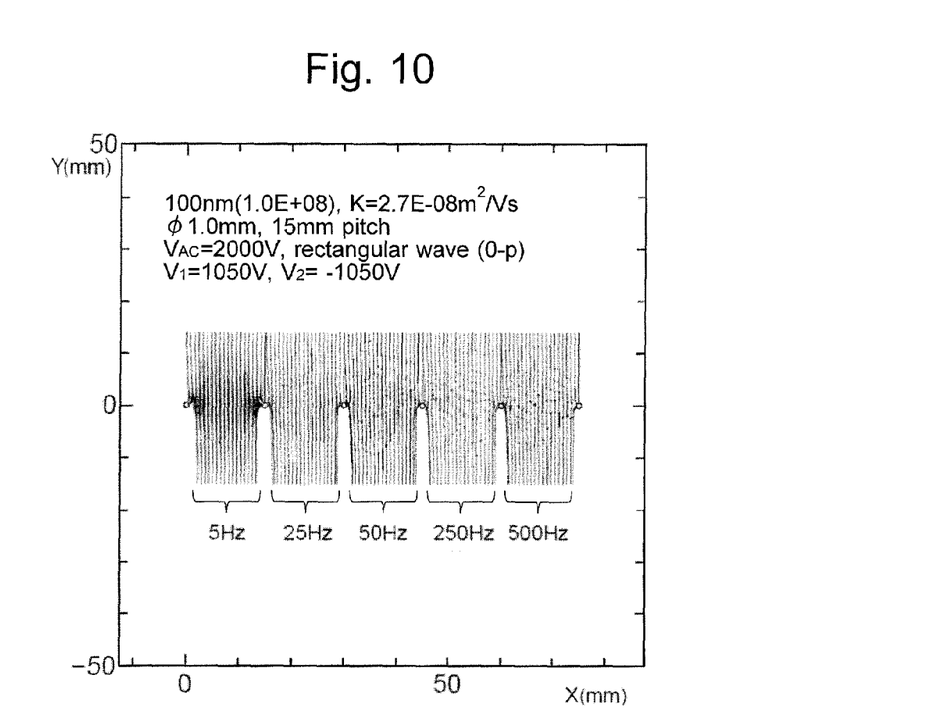
FIG. 10 is a diagram showing the result of a simulation of the trajectory of the charged particle in the present invention.

FIG. 9 shows the result of the simulation for the gas ions, and FIG. 10 shows the result of the simulation for the charged particles. The white circles in these drawings represent the cross section of the electrodes, while the lines in the same drawings represent the trajectories of the gas ions or charged particles. As shown in FIG. 9, the gas ions travelling downward from each position in the space above the electrodes collide with one of the electrodes at any of the aforementioned frequencies of the AC voltage, failing to pass through the gap between the two electrodes. By comparison, in the case of the charged particles travelling downward from each position in the space above the electrodes, as shown in FIG. 10, although a fraction of the particles collide with the electrodes, the largest portion of the particles pass through the gap between the two electrodes without colliding with the electrodes. The result also demonstrates that the ratio of the charged particles colliding with the electrodes decreases with an increase in the frequency of the AC voltage.

REFERENCE SIGNS LIST

10 . . . Gas-Ion Generating Unit
  11 . . . Chamber
  12 . . . Discharge Electrode
  13 . . . Ground Electrode
  14 . . . Discharge Power Source
  15 . . . Gas Introduction Port
  16 . . . Gas-Ion Discharge Port
20 . . . Particle Charging Unit
  21 . . . Chamber
  22 . . . First Upward-Side Opening
  23 . . . Second Upward-Side Opening
  24 . . . First Downward-Side Opening
  25 . . . Second Downward-Side Opening
  26 . . . First Plate Electrode
  27 . . . Second Plate Electrode
  28 . . . Filter
  28a . . . Electrode
  28b . . . Electrode
  29 . . . First Space
  30 . . . Second Space
  31 . . . DC Power Source
  32 . . . First AC Power Source
  33 . . . Second AC Power Source
  34 . . . Carrier Gas Supplier
35 . . . Controller
36 . . . Storage Unit
41 . . . Gas Ion
42 . . . Charged Particle
61 . . . Opposite Electrode
62 . . . Extraction Electrode
63 . . . Opening

The invention claimed is:

1. A particle charger, comprising:
  a) a housing;
  b) a filter composed of a plurality of electrodes extending in a virtual surface partitioning an inside of the housing into a first space and a second space;
  c) a particle introducer for introducing a particle to be charged into the first space;
  d) a gas ion supplier for supplying the first space with a gas ion;
  e) a potential gradient creator for creating a potential gradient within the housing so as to make the gas ion and a charged particle resulting from a contact of the aforementioned particle with the gas ion move from the first space toward the second space;
  f) an AC voltage supplier for applying an AC voltage to each of the electrodes forming the filter, where the voltages applied to any two electrodes neighboring each other among the plurality of electrodes have a phase difference;
  g) a controller for controlling the AC voltage supplier so as to apply, to the plurality of electrodes, voltages which are previously determined so that, among the charged particle and the gas ion moving from the first space toward the second space, the charged particle is allowed to pass through a gap between the electrodes while the gas ion is trapped by one of the electrodes; and
  h) a charged particle extractor for extracting the charged particle admitted to the second space to an outside of the housing.

2. The particle charger according to claim 1, wherein the charged particle extractor produces a stream of carrier gas within the second space and carries the charged particle to the outside of the housing by the stream of carrier gas.

3. The particle charger according to claim 2, wherein the filter is composed of a plurality of rod electrodes arranged parallel to each other.

4. The particle charger according to claim 2, wherein the filter is composed of a plurality of rod electrodes arranged in a form of a grid.

5. The particle charger according to claim 2, wherein the filter is composed of a plurality of circular electrodes arranged in a concentric form.

6. The particle charger according to claim 1, wherein the charged particle extractor creates a potential gradient within the second space in a direction intersecting with the potential gradient and draws the charged particle to the outside of the housing by a motion of the charged particle along the former gradient.

7. The particle charger according to claim 6, wherein the filter is composed of a plurality of rod electrodes arranged parallel to each other.

8. The particle charger according to claim 6, wherein the filter is composed of a plurality of rod electrodes arranged in a form of a grid.

9. The particle charger according to claim 6, wherein the filter is composed of a plurality of circular electrodes arranged in a concentric form.

10. The particle charger according to claim 1, wherein the filter is composed of a plurality of rod electrodes arranged parallel to each other.

11. The particle charger according to claim 1, wherein the filter is composed of a plurality of rod electrodes arranged in a form of a grid.

12. The particle charger according to claim 1, wherein the filter is composed of a plurality of circular electrodes arranged in a concentric form.

* * * * *